US00PP09222P

United States Patent [19]

Svejda

[11] Patent Number: Plant 9,222

[45] Date of Patent: Aug. 1, 1995

[54] SHRUB ROSE PLANT NAMED 'LOUIS JOLLIET'

[75] Inventor: Felicitas J. Svejda, Nepean, Canada

[73] Assignee: Her Majesty the Queen in Right of Canada, as represented by the Minister of Agriculture, Ottawa, Canada

[21] Appl. No.: 215,825

[22] Filed: Mar. 22, 1994

[51] Int. Cl.[6] ..... A01H 5/00
[52] U.S. Cl. ..... Plt./1
[58] Field of Search ..... Plt. 1, 22, 26, 27

[56] References Cited

PUBLICATIONS

Ogilvie, et al., 1992, 'Louis Jolliet' Rose. HortScience 27(3):278.

*Primary Examiner*—Howard J. Locker
*Attorney, Agent, or Firm*—Burns, Doane, Swecker & Mathis

[57] ABSTRACT

A new and distinct variety of shrub rose plant is provided which forms on a continuous basis attractive Roseine Purple blossoms that commonly are borne in clusters. The new variety exhibits a spreading and trailing growth habit with glossy foliage, and good winter hardiness. Resistance to powdery mildew and blackspot has been observed. The new variety propagates well by the use of softwood stem cuttings, and is well adapted for growing as colorful ornamentation in the landscape.

4 Drawing Sheets

SUMMARY OF THE INVENTION

The new variety of shrub rose plant of the present invention was created by artificial pollination during 1984 at the Central Experimental Farm, Ottawa, Ontario, Canada. The female parent (i.e., the seed parent) was *Rosa kordesii* of Breeding Line L83, and the male parent (i.e., the pollen parent) was [(*Rosa kordesii*×(RED DAWN×SUZANNE)×CHAMPLAIN]. Each of the named plants utilized in the breeding program was non-patented in the United States. Selective study carried out at Ottawa, Ontario, Canada, resulted in the identification of a single plant of the new variety.

It was found that the new variety of shrub rose plant of the present invention possesses the following combination of characteristics:

(a) exhibits a spreading and trailing growth habit with glossy foliage,
(b) forms on a generally continuous basis attractive Roseine Purple blossoms,
(c) propagates well by the use of softwood cuttings,
(d) exhibits a good winter hardiness, and
(e) is particularly well suited for growing in the landscape.

The rose plants can be grown well on their own roots out-of-doors without protection at L'Assomption, Quebec, Canada. The blossoms commonly appear continuously from approximately June to October. Resistance to powdery mildew and blackspot is exhibited.

The new variety well meets the needs of the horticulture industry. It can be grown to advantage as attractive ornamentation in parks, gardens, public areas, and residential landscapes. It is particularly well suited for growing in the landscape.

The characteristics of the new variety have been found to be homogenous and stable and have been shown to be strictly transmissible by asexual propagation by the rooting of softwood stem cuttings and by tissue culture conducted at L'Assomption, Quebec, Canada.

The new variety has been named the LOUIS JOLLIET variety.

BRIEF DESCRIPTION OF THE PHOTOGRAPHS

The accompanying photographs show, as nearly true as it is reasonably possible to make the same in color illustrations of this character, typical specimens of plants and plant parts of the new variety. The rose plants of the new variety described herein were approximately 5 to 6 years of age and were photographed during September 1993 while growing on their own roots at L'Assomption, Quebec, Canada. The bloom coloration depicted in the photograph of FIGS. 3 to 7 is believed to be somewhat less accurately depicted than in the other photographs.

FIG. 1—illustrates a group of open flowers, buds, and foliage of the new variety while growing in the landscape, FIG. 2—illustrates an open flower of the new variety with foliage while growing in the landscape, FIG. 3—illustrates a specimen of a young bud of the new variety wherein the sepals are open, FIG. 4—illustrates a specimen of a young flower of the new variety wherein the petals are beginning to open, FIG. 5—illustrates a specimen of a young flower of the new variety as the petals assume a further stage of opening, FIG. 6—illustrates a specimen of a flower of the new variety at a more advanced stage of opening than as illustrated in FIG. 5, FIG. 7—illustrates a specimen of a flower of the new variety at a more advanced stage of opening than as illustrated in FIG. 6, FIG. 8—illustrates a specimen of a fully open flower of the new variety, FIG. 9—illustrates on the left a specimen of a floral receptacle showing the arrangement of the stamens (sepals removed), and on the right of a specimen of a floral receptacle showing the arrangement of the pistils (sepals and stamens removed), FIG. 10—illustrates a specimen of new growth of the new variety, FIG. 11—illustrates the upper surfaces of typical leaves of the new variety with a specimen having seven leaflets being shown on the left, a specimen having five leaflets being shown at the middle, and a specimen having three leaflets being shown on the right, FIG. 12—illustrates the under surfaces of typical leaves of the new variety with a specimen having seven leaflets being shown on the left, a specimen having five leaflets being shown at the middle, and a specimen having three leaflets being shown on the right.

DETAILED DESCRIPTION

Figure 1:
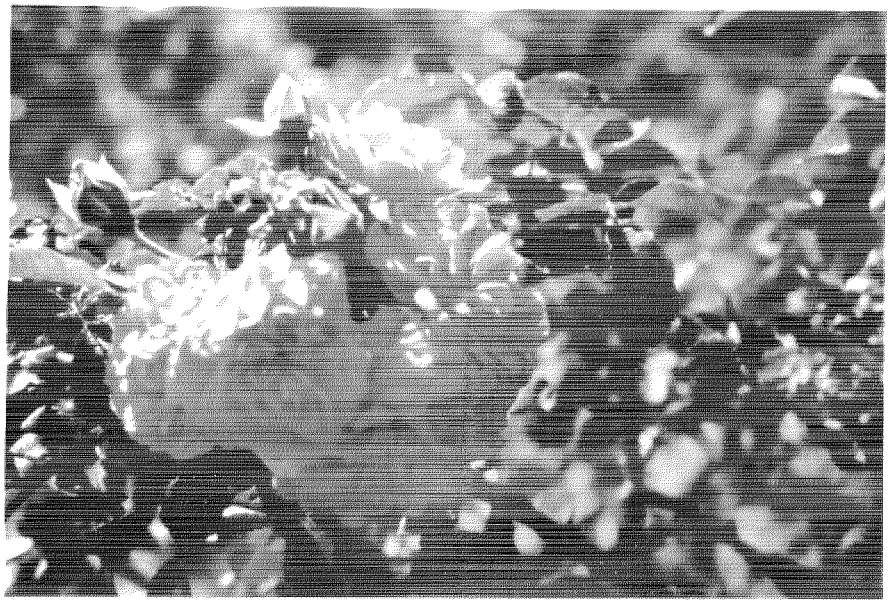
Figure 2:
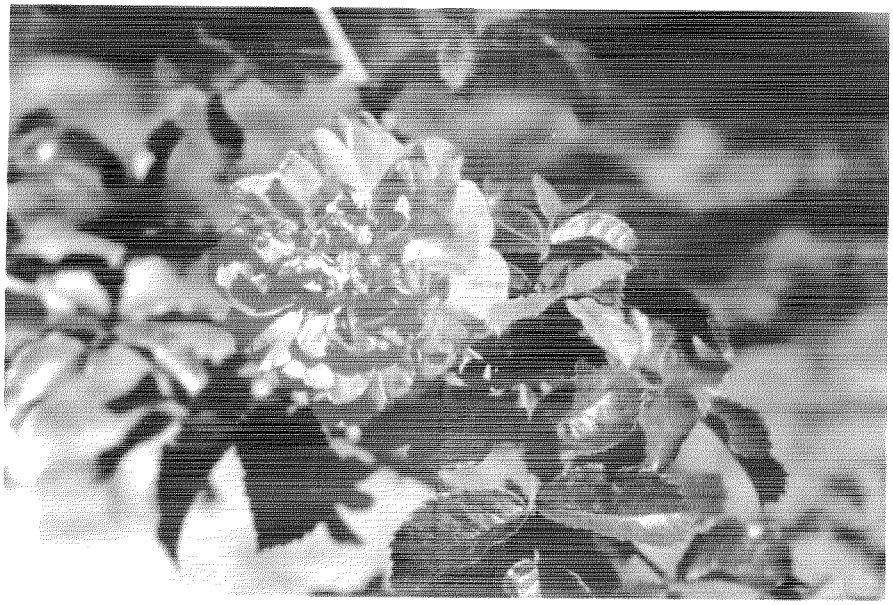
Figure 3:
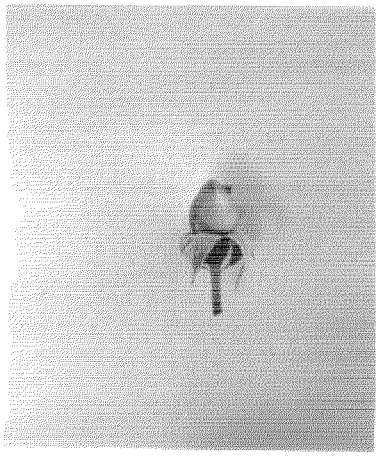
Figure 4:
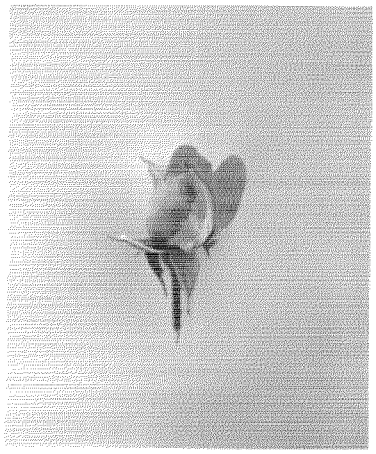
Figure 5:
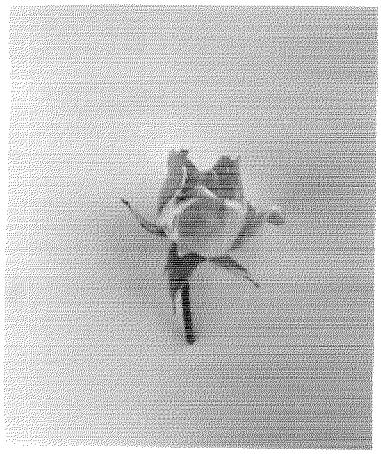
Figure 6:
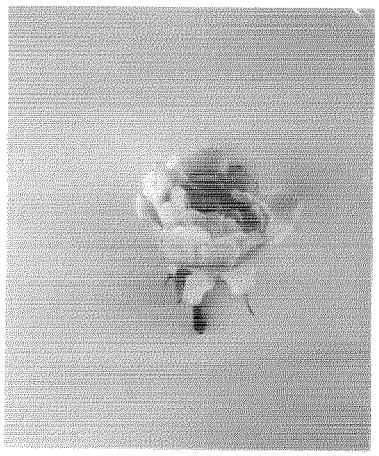
Figure 7:
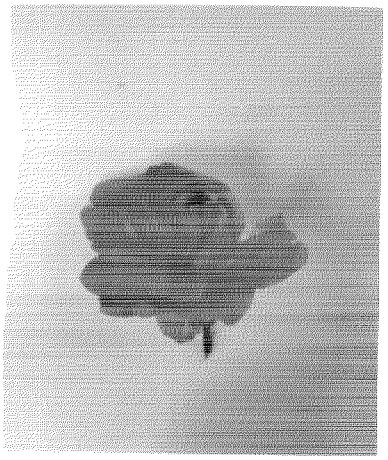
Figure 8:
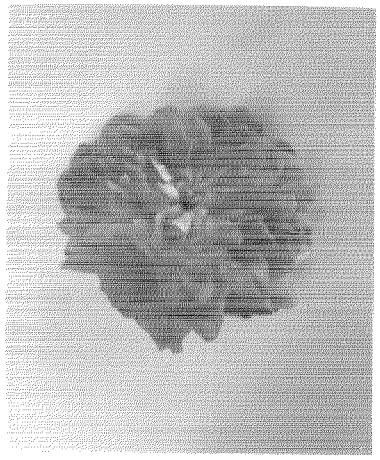
Figure 9:
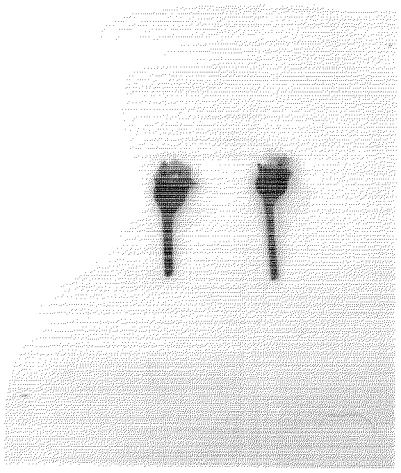
Figure 10:
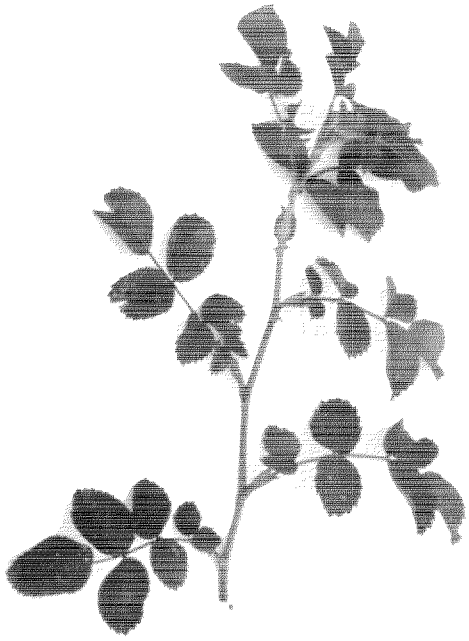
Figure 11:
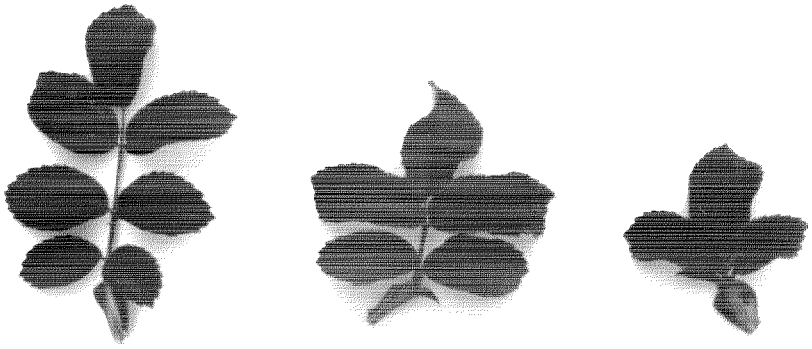
Figure 12:
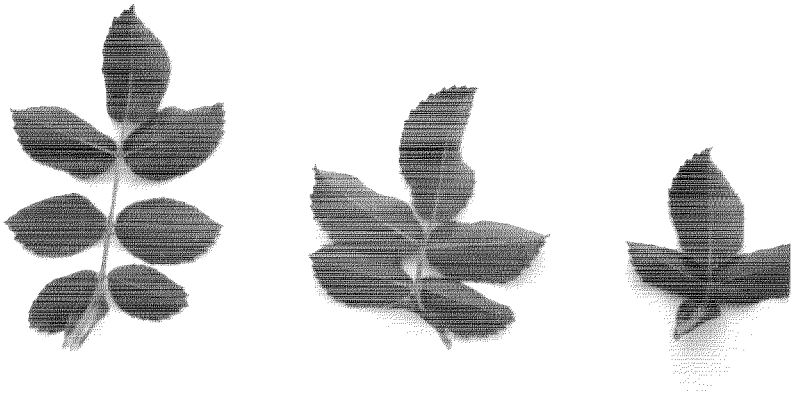

The chart used in the identification of colors is that of the Royal Horticultural Society (R.H.S. Colour Chart). Common color terms are to be accorded their ordinary dictionary significance. The description is based on the observation of 5 to 6 year-old plants of the new variety while being grown outdoors at L'Assomption, Quebec, Canada.

Class: Shrub.

Plant:

*Height.*—Approximately 1.2 meters on average.

*Width.*—Approximately 1 meter on average.

*Habit.*—Spreading and trailing.

Branches:

*Color.*—Young stems: medium green, Green Group 137C, with slightly darker coloration being exhibited under cooler growing conditions. Mature stems: medium green, Green Group 137C, with slightly darker coloration being exhibited under cooler growing conditions.

*Prickles.*—Shape: slightly concave on the upper and under edges. Size: small. Quantity: approximately 18 per 100 mm of stem on average. Color: light green when young and tan when mature.

Leaves: Compound and pinnate.

*Stipules.*—Fairly broad with inwardly facing auricles.

*Petioles.*—Yellow green with red spots when young and medium green with a red tinge when mature.

*Petiolules.*—Very short.

*Leaflets.*—Number: commonly 3, 5 or 7. Shape: rounded base, some are uneven, with acute tip. Serration: single and irregular.

*Color.*—Adult foliage: dark green, both when young and when mature, commonly ranges from Green Group 137A to 137C on the upper surfaces, and commonly is slightly lighter on the under surfaces. General appearance: glossy. Rachis: smooth with very small prickles on the underside.

Inflorescence:

*Number of flowers.*—Usually 3 to 10 per stem.

*Peduncle.*—Erect, light green with a red tinge when young and medium green with a dark red tinge when mature, commonly bear a few small scattered prickles, and approximately 1 to 1.5 cm. in length.

*Sepals.*—Commonly 5 in number, extend beyond the bud on young buds, commonly possess no foliation, light green with a tinge of red when young, and medium green with a tinge of dark red when mature.

Buds.—Shape: ovoid before the opening of the sepals, and progressively becoming globular upon opening. Color upon opening: the outer petals are deep pink.

*Flower.*—Shape: initially cup-shaped and subsequently assumes a flattened configuration (as illustrated). Diameter: approximately 7 cm on average. Color (when blooming): Roseine Purple, approaching Red-Purple Group 68A, on upper surface, and lighter on the under surface, approaching Red-Purple Group 68D with gradual fading. The bloom coloration is somewhat mottled both when young and when mature, and tends to lighten as the blooms mature. Fragrance: medium spicy. Petal number: approximately 35 to 55 on average. Petal texture: velvety. Lasting quality: the blossoms last approximately 4 to 7 days while present on the plant under most growing conditions. Petal drop: some petals may adhere to the receptacle. Anthers: gold in coloration. Pollen: yellow in coloration. Filaments: yellow-green in coloration. Receptacle: globular in configuration, green in coloration with the formation of purple hips.

Development:

*Vegetation.*—Intermediate vigor.

*Blossoming.*—Generally continuous from approximately June to October.

*Hardiness.*—Survives consistently without cover in Eastern Canada (Zone 4, Quellet and Sherk, 1967).

*Resistance to diseases.*—Highly resistant to powdery mildew and blackspot.

*Preferred mode of propagation.*—The use of softwood cuttings to produce self-rooted plants is recommended for the production of quality cold-tolerant plants.

1. A new and distinct variety of shrub rose plant characterized by the following combination of characteristics:

(a) exhibits a spreading and trailing growth habit with glossy foliage,
(b) forms on a generally continuous basis in clusters attractive Roseine Purple blossoms,
(c) propagates well by the use of softwood cuttings,
(d) exhibits a good winter hardiness, and
(e) is particularly well suited for growing in the landscape;

substantially as herein shown and described.

* * * * *